United States Patent
Takahashi et al.

(10) Patent No.: US 6,250,137 B1
(45) Date of Patent: Jun. 26, 2001

(54) METHOD AND APPARATUS FOR DETERMINING GASOLINE CHARACTERISTICS BY USING ULTRASONIC WAVE

(75) Inventors: Toshimitsu Takahashi; Takuya Kondo; Hiroaki Saitou; Toshihiro Okazaki, all of Susono; Mamoru Ishikiriyama, Mishima, all of (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/464,385

(22) Filed: Dec. 16, 1999

Related U.S. Application Data

(62) Division of application No. 08/941,275, filed on Sep. 30, 1997, now Pat. No. 6,032,516.

(30) Foreign Application Priority Data

Oct. 8, 1996 (JP) .................................... 8-267155
Apr. 14, 1997 (JP) .................................... 9-095694

(51) Int. Cl.$^7$ ................................................. G01N 29/02
(52) U.S. Cl. ........................................ 73/64.53; 73/61.49
(58) Field of Search ...................... 73/61.45, 61.49, 73/61.79, 64.53, 579, 596, 597, 599, 602

(56) References Cited

U.S. PATENT DOCUMENTS

| | | |
|---|---|---|
| 3,859,846 | 1/1975 | Asada et al. . |
| 4,320,659 | 3/1982 | Lynnworth et al. . |
| 4,565,088 | 1/1986 | Crambes . |
| 4,779,452 | 10/1988 | Cohen-Tenoudji et al. . |
| 5,060,507 | 10/1991 | Urmson et al. ..................... 73/24.01 |
| 5,255,564 | 10/1993 | Glad et al. .............................. 73/597 |
| 5,263,371 | * 11/1993 | Maresca, Jr. et al. ............. 73/290 V |
| 5,271,267 | * 12/1993 | Baumoel .............................. 73/32 A |
| 5,627,323 | * 5/1997 | Stern ................................. 73/861.28 |
| 5,644,090 | * 7/1997 | Spendel ............................ 73/861.27 |
| 5,739,432 | 4/1998 | Sinha . |
| 5,869,745 | * 2/1999 | Schroeder et al. ................. 73/31.04 |
| 5,886,262 | 3/1999 | Sinha ..................................... 73/579 |

FOREIGN PATENT DOCUMENTS 7-225228    8/1995 (JP) .

OTHER PUBLICATIONS

Susumu Sakagami, et al. "Fuel Property Detection Using Fuel Density", Automobile Technical Institute, No. 952, May 1995, pp. 199–202.

* cited by examiner

*Primary Examiner*—Helen Kwok
(74) *Attorney, Agent, or Firm*—Oblon, Spivak, McClelland, Maier & Neustadt, P.C.

(57) ABSTRACT

The present invention relates to the measurement of gasoline volatility characteristics, and is directed in particular to the provision of an ultrasonic-type gasoline characteristic determination method and apparatus capable of determining the volatility characteristics with good accuracy by measuring the velocity of an ultrasonic wave in a gasoline containing alcohol or other additives and by compensating for deviations from a reference temperature, and a method for determining gasoline volatility characteristics by using an ultrasonic wave is provided, comprising the steps of transmitting an ultrasonic wave into a gasoline being measured, measuring the velocity of the ultrasonic wave in the gasoline, and determining the volatility characteristics of the gasoline from the velocity.

2 Claims, 8 Drawing Sheets

Fig. 5(a).1

METHOD AND APPARATUS FOR DETERMINING GASOLINE CHARACTERISTICS BY USING ULTRASONIC WAVE

This application is a Division of application Ser. No. 08/941,275 filed on Sep. 30, 1997, now U.S. Pat. No. 6,032,516.

BACKGROUND OF THE INVENTION

1. Field of the Invention

The present invention relates to the measurement of gasoline volatility characteristics, and more particularly to an ultrasonic-type gasoline characteristic determination method and apparatus capable of determining the volatility characteristics with good accuracy by measuring the velocity of an ultrasonic wave in a gasoline containing alcohol or other additives and by compensating for deviations from a reference temperature.

2. Description of the Prior Art

Among the characteristics of automotive gasolines, the ability to resist knocking in engines is one of the important quality-determining characteristics. To increase this anti-knocking ability, tetra ethyl lead (TEL) is added, but in recent years, gasolines containing about 10% ethyl alcohol instead of TEL have been used in the United States and other countries.

Gasoline, in itself, is not always uniform, but there are variations in its volatility (combustion properties). The T50 value used to describe this volatility indicates the temperature at which 50 percent of the gasoline evaporates, the T50 value being lower for lighter gasolines. In accordance with this T50 value, i.e., volatility, engine control must be optimized. For example, if the volatility before engine startup can be determined, it becomes possible to minimize the amount of fuel increase during engine startup and thus reduce emissions during the startup.

In particular, gasolines used in the United States have varying degrees of volatility, and it is essential to optimize engine control according to the volatility. The need therefore arises for a sensor capable of monitoring gasoline volatility. The T50 value that serves as a measure of gasoline volatility is estimated from gasoline density. This density is calculated from the propagation time of an ultrasonic wave.

In Japanese Unexamined Patent Publication (Kokai) No. 7-225228 as one prior art pertaining to this field, a detection device is installed midway through a gasoline pipeline, and noting the fact that gasoline volatility tends to become higher for softer gasolines with lower densities, the propagation delay time of an ultrasonic wave is detected to obtain the gasoline density, thus measuring its volatility properties and estimating the T50 value.

This method, however, has not been sufficient in terms of accuracy since for gasolines containing additives such as alcohol, the relationship between the density and the T50 value is not constant but an inversion occurs. There is therefore a need for a simple gasoline property determination method and apparatus with improved accuracy.

SUMMARY OF THE INVENTION

An object of the present invention is to study a method that involves measuring the velocity of an ultrasonic wave to determine the volatility of gasoline containing alcohol or other additives, and to provide an ultrasonic-type gasoline characteristic determination method and apparatus that are free from deviations of the kind inherent in the prior art which relies on the relationship between density and T50 value, and that achieve high accuracy.

Another object of the invention is to study ways of compensating for temperatures at the time of measurement in the above determination method, and to provide an ultrasonic-type gasoline characteristic determination method and apparatus that enable the variation with temperature of the propagation distance of an ultrasonic wave to be cancelled by utilizing the resonance characteristic or the reflected wave strength of the ultrasonic wave.

A further object of the invention is to study ways of compensating for temperatures at the time of measurement in the above determination method, and to provide an ultrasonic-type gasoline characteristic determination method and apparatus that enable the variation with temperature of the propagation distance of an ultrasonic wave to be cancelled by utilizing a thermal contraction spring or the expansion of a gas and thereby varying the propagation distance of the ultrasonic wave.

The gist of the present invention is summarized as follows:

(1) An ultrasonic-type gasoline characteristic determination method for determining gasoline volatility characteristics by using an ultrasonic wave, comprising the steps of transmitting an ultrasonic wave into a gasoline being measured, measuring the velocity of the ultrasonic wave in the gasoline, and determining the volatility characteristics of the gasoline from the velocity.

(2) An ultrasonic-type gasoline characteristic determination method according to item (1), wherein the volatility characteristics of the gasoline are determined after temperature-compensating the velocity of the ultrasonic wave against a reference temperature.

(3) An ultrasonic-type gasoline characteristic determination method according to item (2), wherein the temperature compensation is performed by measuring the resonant frequency of a substance immersed in the gasoline.

(4) An ultrasonic-type gasoline characteristic determination method according to item (2), wherein the temperature compensation is performed by measuring the reflected wavestrength of the ultrasonic wave in the gasoline.

(5) An ultrasonic-type gasoline characteristic determination method according to item (2), including the steps of transmitting an ultrasonic wave into a gasoline being measured as well as into a reference substance, measuring the velocity of the ultrasonic wave in the gasoline and the reference substance, and temperature-compensating the velocity of the ultrasonic wave in the gasoline against the reference temperature on the basis of the velocity of sound in the reference substance, and including distance varying means for correcting distance on the basis of the temperature-compensated ultrasonic wave velocity.

(6) An ultrasonic-type gasoline characteristic determination method according to item (3), wherein the substance immersed in the gasoline is a transducer.

(7) An ultrasonic-type gasoline characteristic determination apparatus for determining gasoline volatility characteristics by using an ultrasonic wave, comprising a transducer for transmitting and receiving an ultrasonic wave in a gasoline, and distance varying means for correcting the distance between the transmission and reception of the ultrasonic wave on the basis of the temperature of the gasoline.

(8) An ultrasonic-type gasoline characteristic determination apparatus according to item (7), including a first reflecting plate constructed from a low thermal expansion member and a second reflecting plate constructed from a high thermal expansion member, for reflecting ultrasonic waves transmitted from an ultrasonic wave transmitter, ultrasonic wave receiving means for receiving the ultrasonic waves reflected from the first reflecting plate and the second reflecting plate, means for detecting the propagation times of the waves reflected from the first reflecting plate and the second reflecting plate, and thereby obtaining an ultrasonic wave velocity temperature-compensated against a reference temperature, and means for detecting the volatility characteristics of the gasoline from the temperature-compensated ultrasonic wave velocity.

BRIEF DESCRIPTION OF THE DRAWINGS

FIG. 5(a) shows a separate setup for a known substance, and FIG. 5(b) shows an integral setup.

FIG. 8(a) shows the relationship between resonant frequency and impedance, FIG. 8(b) the relationship between temperature and resonant frequency, FIG. 8(c) the relationship between temperature and impedance at resonant frequency, and FIG. 8(d) the relationship between temperature and reflection strength.

FIG. 9(a) shows a temperature compensation method according to a fifth example, FIG. 9(b) shows another example of the temperature compensation method according to the fifth example, and FIG. 9(c) shows a temperature compensation method according to a fourth example.

FIG. 10(a) shows a prior art method without temperature compensation, FIG. 10(b) shows a temperature compensation method using a high thermal contraction spring, and FIG. 10(c) shows a temperature compensation method using a bimetal.

FIG. 11(a) shows a method using a low thermal expansion member and a high thermal expansion member, and FIG. 11(b) shows a method using a low thermal expansion member and a high thermal expansion member.

DESCRIPTION OF THE PREFERRED EMBODIMENT

Figure 3:
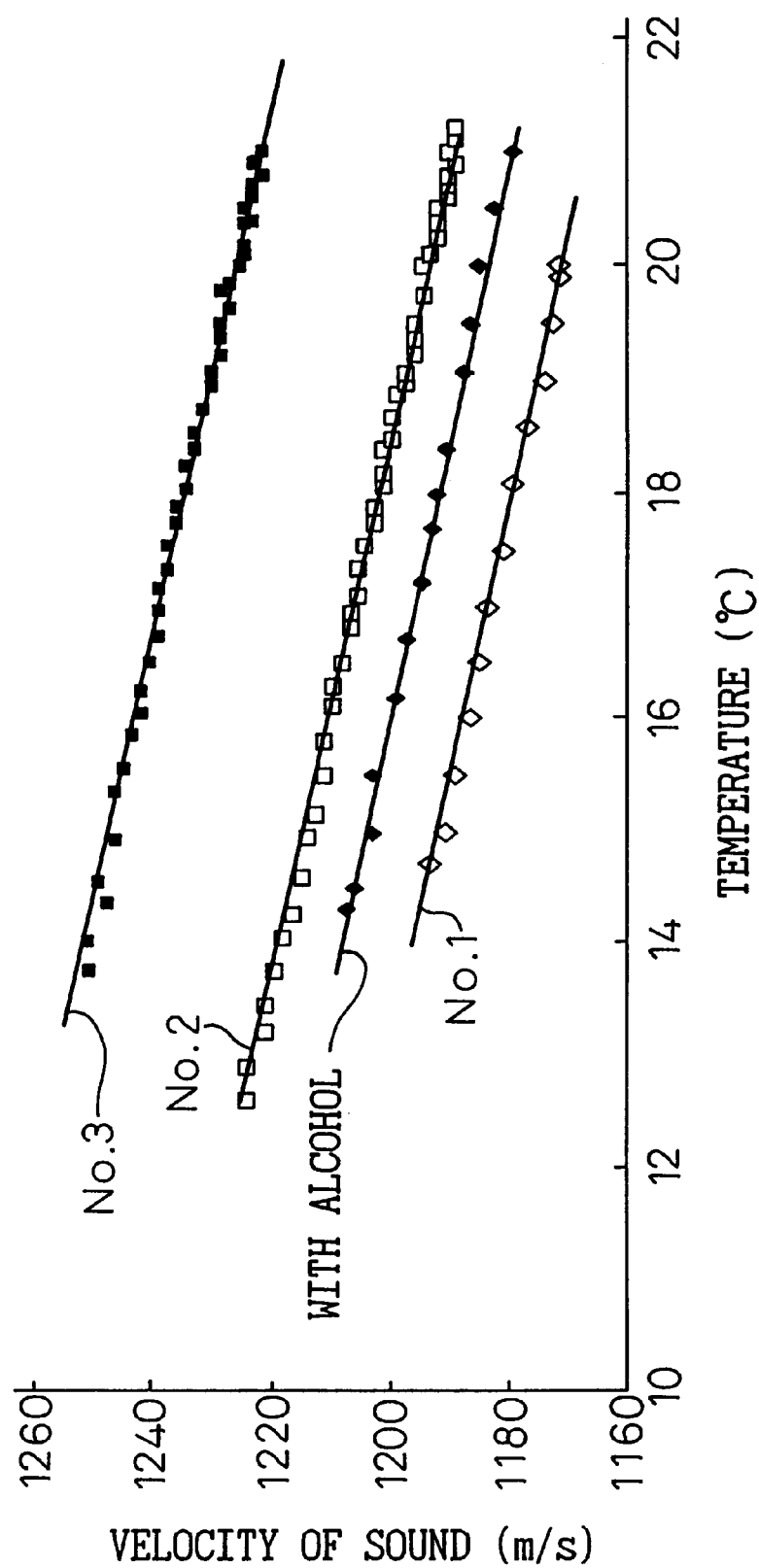
FIG. 3 is a diagram showing the relationship between the velocity of sound in gasoline and the temperature at the time of measurement, according to the present invention.

Since the velocity of sound in a gasoline varies with temperature as shown in FIG. 3, if the T50 value (the temperature at which 50% by volume evaporates), a parameter of gasoline volatility, is to be estimated from the velocity of sound in the gasoline, the value of sound velocity at a reference temperature must be determined. To achieve this, previously, it has been necessary to provide a sound velocity measuring sensor for measuring gasoline temperature at the time of sound velocity measurement in a temperature sensor, such as a thermocouple or a thermistor, and to make corrections with respect to the reference temperature. According to the present invention, on the other hand, the volatility characteristics of gasoline can be detected from the velocity of an ultrasonic wave in a simple manner and with good accuracy.

The present invention will be described in detail below with reference to the accompanying drawings.

In the embodiments described hereinafter, the velocity of sound is measured with the illustrated apparatus immersed in a gasoline (the gasoline is not shown).

Figure 5A:
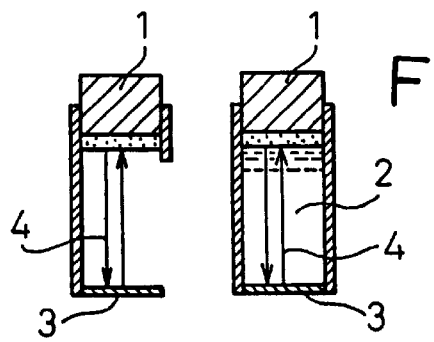
FIGS. 5(a) and 5(b) show methods for temperature-compensating the velocity of sound in gasoline according to a first example of the present invention.

A schematic diagram outlining the measurement of ultrasonic wave velocity is shown in the left side of FIG. 5(a) (in an example) described later. An ultrasonic wave 4 of a prescribed frequency is transmitted from a transducer 1 into the gasoline, and the wave reflected from a reflecting surface 3 is received. The round trip time, t, of the ultrasonic wave 4 propagated through the gasoline is measured, and the distance L is divided by t to determine the velocity of sound in the gasoline. For the measurement of ultrasonic wave velocity, generally the propagation speed of an ultrasonic wave can be expressed by $v=(K/d)^{1/2}$ (where v: velocity of ultrasonic wave, d: gasoline density, K: bulk modulus). At this time, since K tends to increase with increasing density, by keeping K at reasonably large values the relationship between propagation speed v and T50 can be maintained uniform as shown in FIG. 1 even when the density decreases.

Figure 1:
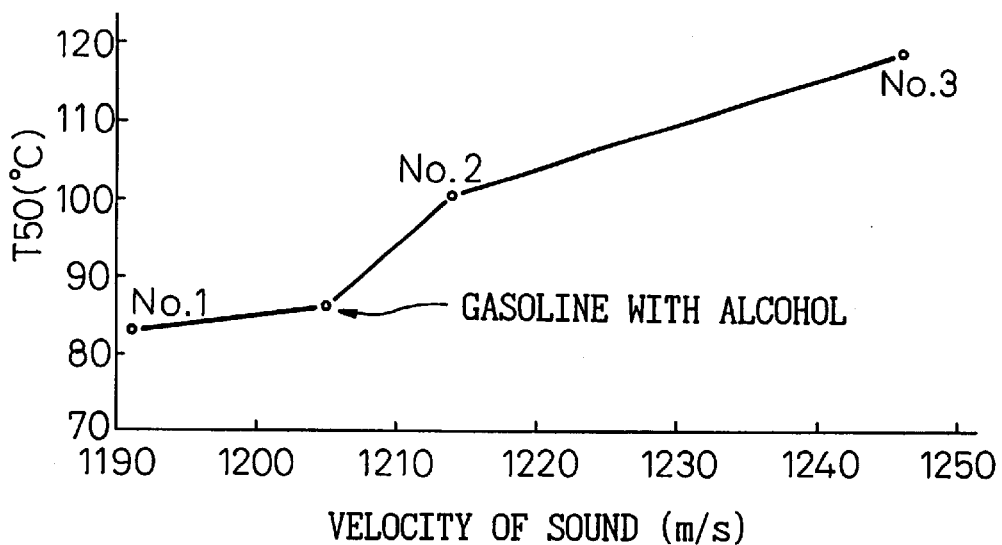
FIG. 1 is a diagram showing the relationship between the velocity of sound in gasoline and T50 value, according to the present invention.
Figure 2:
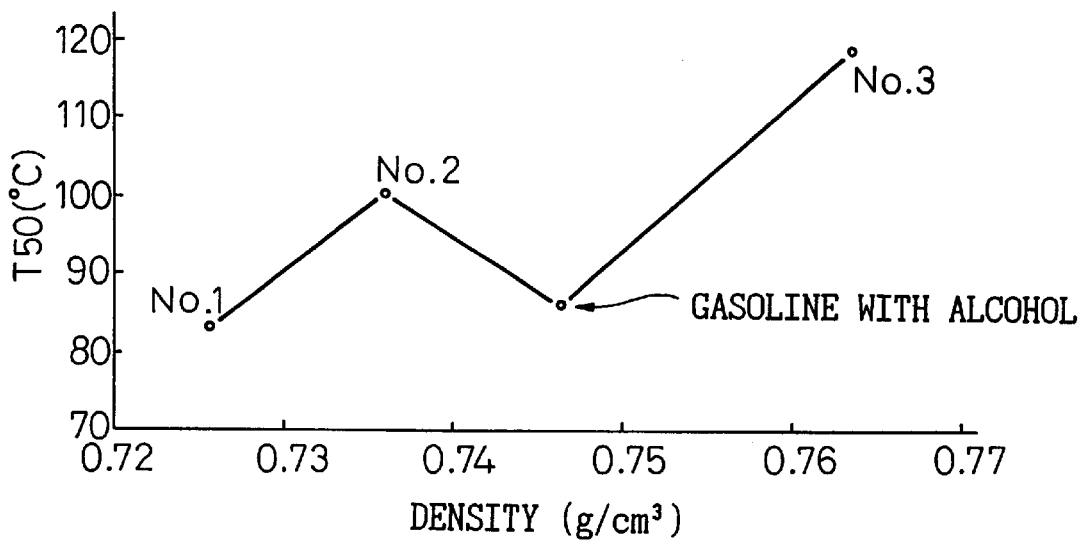
FIG. 2 is a diagram showing the relationship between density in gasoline and T50 value, according to the prior art.

In FIG. 1, the relationship between the velocity of sound and T50 is plotted collectively for three kinds of gasolines and a gasoline with alcohol; as shown, an abnormal point due to the addition of alcohol is not observed that was seen in the density-T50 relationship in the prior art as shown in FIG. 2. In other words, the sound velocity-T50 relationship in a gasoline is free from the inversion inherent in the density-T50 relationship, and the accuracy of detection can thus be improved.

On the other hand, in the prior art method in which the density is calculated from the propagation distance of an ultrasonic wave, only the propagation distance is used for determination, assuming that the distance is constant. In reality, however, the propagation time varies with the temperature at the time of measurement. This is because of the temperature characteristic of the substance being measured, and the propagation distance, change due to the thermal expansion of the measuring device used. If the velocity of sound is used as previously described, the variation in propagation distance due to thermal expansion can be cancelled by dividing the propagation distance after the variation with the propagation time after the variation. It is believed here that the T50 value representing volatility has a correlation with the molecular weights and the intermolecular bonding forces of gasoline components, and also that the molecular weights and intermolecular forces are related to the density and bulk modulus (the velocity of sound is a function of density and bulk modulus).

Usually, as shown in FIG. 3, changes in the temperature at the time of measurement entail changes due to the temperature dependence of a substance being measured, and the velocity of sound varies with temperature. FIG. 3 shows that the velocity of sound decreases with increasing temperature for the three kinds of gasolines as well as the gasoline with alcohol. To evaluate the characteristics, therefore, it is necessary to obtain the velocity of sound at a reference temperature in order to make the evaluation. As can be seen from FIG. 3, since the velocity of sound varies linearly with a nearly equal slope for any gasoline, the velocity of sound can be approximated by a straight line and can be expressed by its slope and intercept. If the deviation from the reference temperature is known, the velocity of sound at the reference temperature can be determined based on this straight line.

The examples of the present invention will now be described in detail below.

EXAMPLES

Example 1

This example relates to a method in which the temperature is determined from the value of sound velocity in a substance whose sound velocity versus temperature characteristic is known and, based on the result, T50 is measured.

FIG. 5(*a*) shows a schematic diagram of the apparatus according to the present example. An ultrasonic transmitter/receiver of the transducer is immersed in the gasoline, and the temperature of the known substance is set equal to that of the gasoline. Next, ultrasonic waves are transmitted from the transducer simultaneously into the gasoline and the known substance, and the temperature of the known substance is measured from the sound velocity versus temperature characteristic of the known substance. From this value, the temperature in the gasoline is determined. Using the sound velocity-temperature relationship of the gasoline, the value of sound velocity at the reference temperature is calculated from the temperature and sound velocity at the time of the measurement.

More concretely, the ultrasonic wave transmitted from the transducer 1 is propagated through the gasoline being measured, and is reflected from the reflecting surface and received by the transducer 1. The sound velocity in the gasoline being measured can be obtained by dividing the propagation distance with the propagation time. Moreover, concurrently, and simultaneously, an ultrasonic wave is transmitted from the transducer 1 into a substance (gasoline, or octane or the like as a kind of gasoline) enclosed in circumference, and the value of sound velocity is obtained in the same manner. The temperature at the time of the measurement is the same for both cases. Further, if the construction such as shown in FIG. 5(*b*) is adopted, ultrasonic waves can be transmitted and received in the gasoline being measured and the substance known as sound velocity versus temperature characteristic by using a single transducer; this construction does not require the provision of a temperature sensor such as a thermocouple, and contributes to a reduction in the cost.

Figure 4:
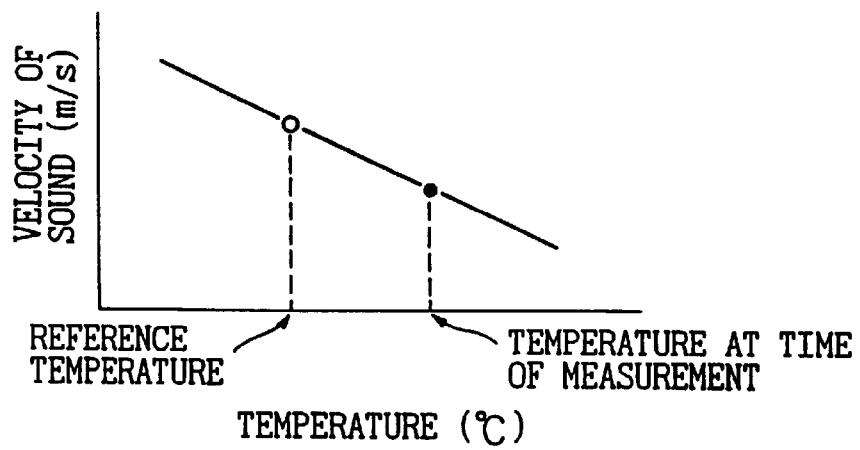
FIG. 4 is a diagram showing the velocity of sound versus temperature characteristic of gasoline, according to the present invention.
Figure 7:
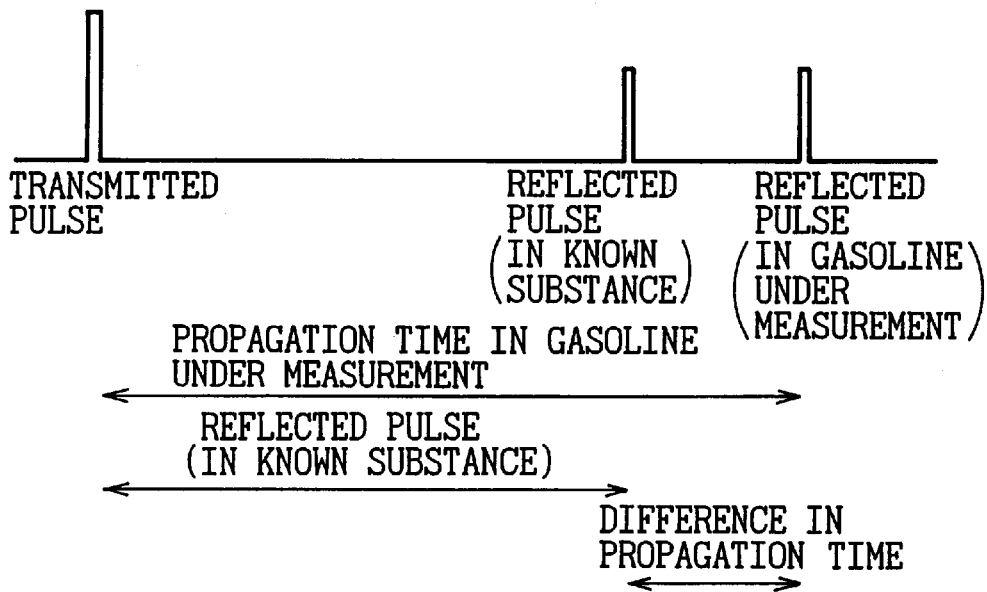
FIG. 7 is a diagram showing a method for temperature-compensating the velocity of sound in gasoline when a liquid or an equivalent substance is used as the known substance according to the first example in the present invention.
Figure 8A:
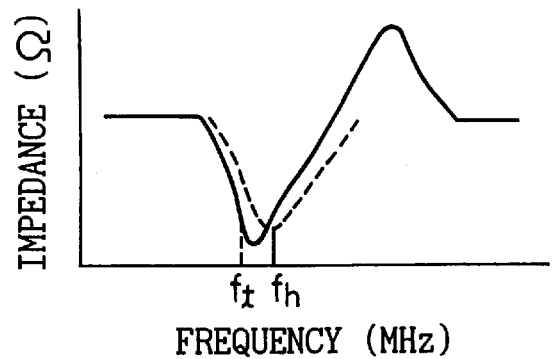
FIGS. 8(a)–8(d) show methods for temperature-compensating the velocity of sound in gasoline according to a second example of the present invention.
Figure 8B:
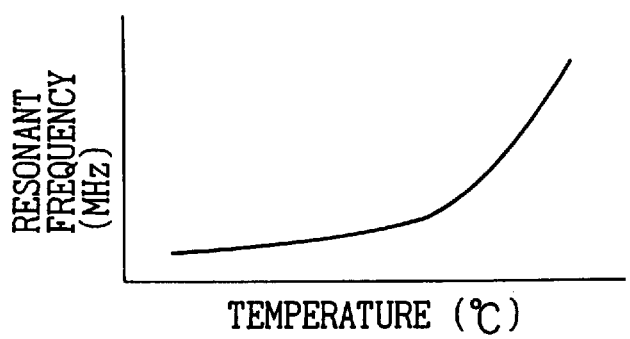
Figure 8C:
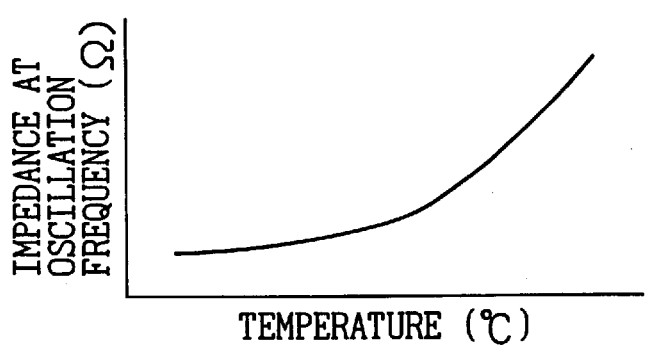
Figure 8D:
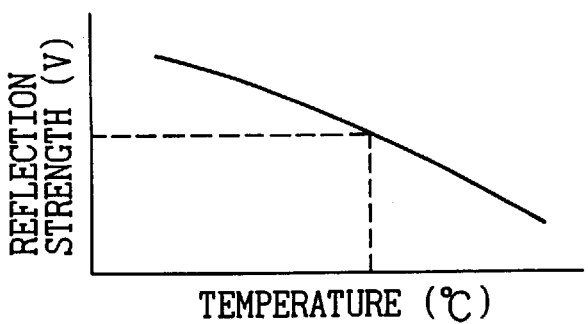

In this example, a substance whose sound velocity versus temperature characteristic is known, as shown in FIG. 4 and is, for example, a liquid such as an octane, is used as the known substance, and the velocity of sound at the reference temperature can be calculated by obtaining the velocity of sound from the propagation time in the gasoline under measurement, and the temperature from the propagation time in the known substance, as shown in FIG. 7. Since the change in propagation time is large compared with the change in temperature, the sound velocity-temperature change rate can be set larger than for a solid and a high resolution of the propagation time is not required. Further, by appropriately selecting a known substance, for example, a liquid such as a gasoline or gasoline fraction, the value of sound velocity can be made smaller than for a solid (a metal), making it possible to increase the propagation time.

In this embodiment, if a substance (decane or the like) having approximately the same sound velocity-temperature changing ratio as the gasoline is used as the reference substance, the value of sound velocity in the gasoline at the reference temperature can be measured by only measuring the difference in propagation time between that substance and the gasoline being measured.

Figure 6:
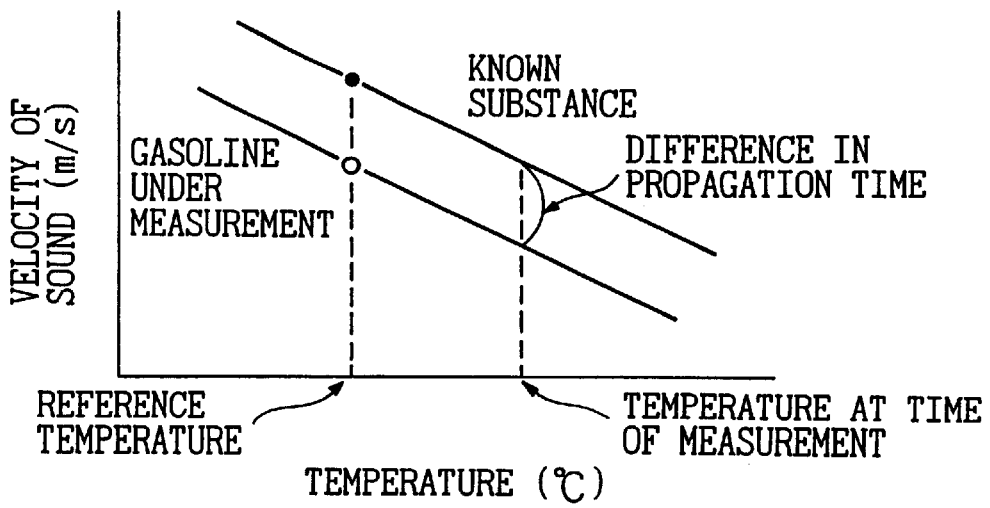
FIG. 6 is a diagram showing a method for temperature-compensating the velocity of sound in gasoline when an equivalent substance is used as the known substance according to the first example in the present invention.

This will be explained with reference to FIGS. 6 and 7. As shown in FIG. 7, the difference of the propagation time is obtained between the reflected pulses. In this case, ultrasonic waves are transmitted from the transducer 1 into the gasoline and the known substance 2, and the difference in sound velocity is calculated from the difference between the propagation time in the gasoline being measured and the propagation time in the known substance; then, the value of sound velocity in the gasoline under measurement is calculated from the value of sound velocity in the known substance at the reference gasoline and from the difference in sound velocity.

Example 2

This example relates to a method in which T50 is measured based on the temperature dependence of the resonance frequency of the transducer.

The velocity of sound is measured from the propagation time of the ultrasonic wave through the gasoline being measured, in the same manner as in the first example. At the same time, the resonant frequency ($f_h$) corresponding to the oscillation frequency ($f_1$) is measured from the transducer's resonance characteristic shown in FIG. 8(*a*). This resonant frequency varies with temperature, as shown in FIG. 8(*b*); therefore, by measuring the resonant frequency, the temperature at the time of sound velocity measurement can be obtained, and the velocity of sound at the reference temperature can thus be calculated. More specifically, the sensor transmitter and receiver are set into the gasoline. The temperature of the transducer at this time is set equal to that of the gasoline. The resonant frequency of the transducer rises as the temperature rises, and the impedance at its oscillation frequency also rises with increasing temperature. Here, the oscillation frequency $f_1$ is assumed to be a resonant frequency at a temperature lower than the operating environment range of the gasoline.

With oscillation at $f_1$, the impedance increases with increasing temperature, in accordance with which the incident wave strength decreases, and so does the reflected wave strength. This relationship is shown in FIG. 8(*d*), using which the temperature of the gasoline is obtained from the reflected wave strength.

Accordingly, using the value of the simultaneously measured sound velocity in the gasoline and the sound velocity-temperature relationship of the gasoline, the value of sound velocity at the reference temperature can be calculated from the temperature and sound velocity at the time of the measurement.

Example 3

Figure 5B:
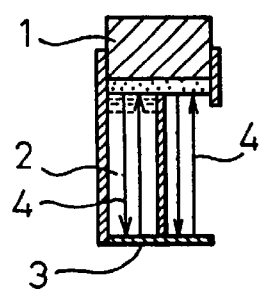

This example relates to a method in which the temperature is measured from the reflection strength in the known substance. In this example, the temperature of the gasoline can be measured by measuring the strength of the ultrasonic wave transmitted through the known substance. As shown in FIG. 5(b) previously mentioned, an ultrasonic wave is transmitted into the known substance, and the strength of the reflected wave received by the transducer is measured.

This acoustic impedance is the product of density and sound velocity as shown in the following formula, and its value varies with temperature. The temperature can therefore be measured by measuring the acoustic impedance, i.e., the strength of the reflected wave.

Acoustic impedance (Z)=Density ($\rho$)×Sound velocity (C)

$\rho$: g/cm$^3$

Reflected wave strength: m/sec

Reflected wave strength $\alpha$ Acoustic impedance (Z)

More concretely, the transducer transmitter and receiver are set into the gasoline, and the temperature of the transducer and known substance at this time is set equal to that of the gasoline. The resonant frequency of the transducer rises as the temperature rises. On the other hand, the acoustic impedance ($\rho$C) decreases as the temperature rises. As a result, the difference from ($\rho$C) of the transducer increases, decreasing the ultrasonic transmittance of the known substance as shown in the following formula. Consequently, it is difficult to transmit the ultrasonic wave, and the strength of the reflected ultrasonic wave decreases. Thus the temperature of the gasoline can be measured by measuring the strength of the reflected wave in the known substance.

Transmittance=$4Z_1Z_2/(Z_1+Z_2)^2$ $Z_1$: $\rho$C of the transducer $Z_2$: $\rho$C of the known substance Thus, using the value of the simultaneously measured sound velocity in the gasoline and the sound velocity-temperature relationship of the gasoline, the value of sound velocity at the reference temperature can be calculated from the temperature and sound velocity at the time of the measurement.

Example 4

Figure 9C:
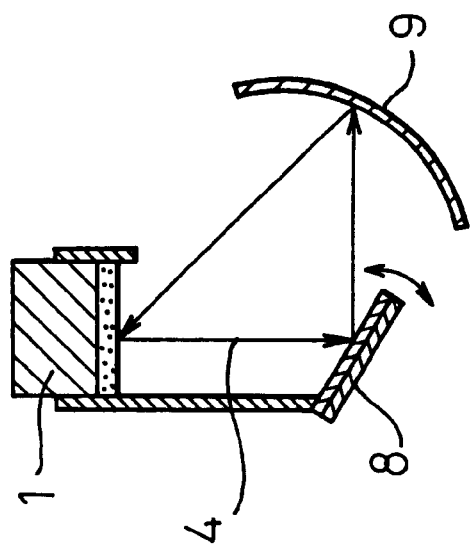
FIGS. 9(a)–9(c) show methods for temperature-compensating the velocity of sound in gasoline according to embodiments of the present invention.

This example relates to a method in which the propagation distance of the ultrasonic wave is varied with varying temperature by using a bimetal and a concave reflecting surface. This example uses the technique of varying the distance to the reflecting surface with varying temperature as a method for cancelling the variation with temperature of the sound velocity in the gasoline. The changing ratio of the distance with temperature (coefficient of thermal expansion) necessary for this technique is three orders of magnitude greater than the coefficient of thermal expansion of iron or aluminum. An outline of this example is illustrated in FIG. 9(c). The ultrasonic wave 4 transmitted from the transducer 1 is reflected by the bimetallic reflecting plate 8 and then reflected by the concave reflecting surface 9 back to the transducer 1 for reception. Here, the bimetallic reflecting plate 8 is constructed so that the angle of reflection is varied with varying temperature. The variation with temperature of the value of sound velocity can be cancelled by varying the propagation distance of the ultrasonic wave from the transducer back to the transducer via the bimetallic reflecting plate and the concave reflecting surface in such a manner as to cancel the variation of the ultrasonic wave with temperature.

Example 5

Figure 9B:
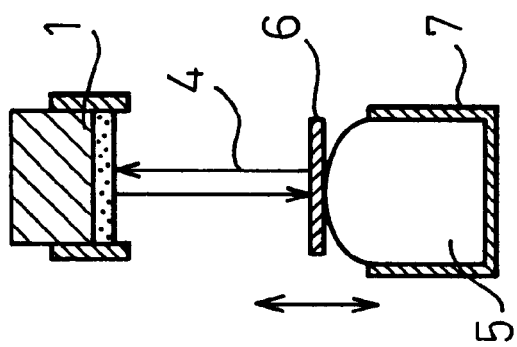

This example relates to a method in which the propagation distance of the ultrasonic wave is varied with varying temperature by utilizing the thermal expansion of a gas. In this embodiment, the variation of the sound velocity is cancelled by varying the propagation distance of the ultrasonic wave, as in the fourth example. An outline is illustrated in FIG. 9(b). A hermetically sealed gas container 7 (constructed of material having good thermal conductivity, such as copper, except the top which is made of an elastically expansible material) is placed under a reflecting plate 6. The gas 5 hermetically sealed in the container expands and contracts considerably with a relatively small change in the temperature of the gasoline being measured; therefore, by making a setup to accommodate the expansion and contraction with the thermal expansion coefficient, Young modulus, etc. of the elastically expansible material, the container top surface, i.e, the reflecting surface, can be moved up and down in such a manner as to cancel the sound velocity. That is, the distance to the reflecting surface can be varied with varying temperature to cancel the variation with temperature of the value of sound velocity.

Figure 9A:
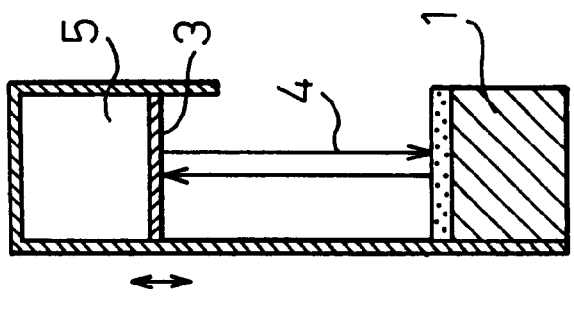

More specifically, the transmitter/receiver of the transducer 1 shown in FIG. 9(a) is immersed in the gasoline. The ultrasonic wave 4 transmitted from the transducer 1 propagates through the gasoline toward the reflecting surface 3. On the other hand, the reflecting surface is moved up or down by the thermal expansion of the gas, thus changing the propagation distance and thereby cancelling the variation of the sound velocity with temperature. The changing ratio of the distance with temperature to the reflecting surface and the design of the hermetically sealed gas container are determined by the following formulas.

The temperature-volume changing ratio of the gas container is V/T=V+$\Delta$V/T+$\Delta$T according to the Boyle-Charles's law; hence, $\Delta$V/$\Delta$T=V/T. Here, denoting the volume at the reference temperature by V, A×B=V, where A is the cross section and B is the height. On the other hand, denoting the distance to the reflecting surface by L, (a•L)/(−a•T+b)•A= V/T=A×B/T; transforming this, we obtain B=(a•L•T)/(− a•T+b).

Example 6

Figure 10A:
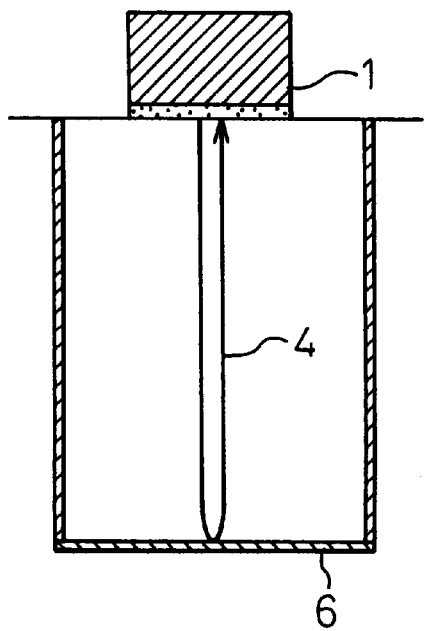
FIGS. 10(a)–10(c) show methods for temperature-compensating the velocity of sound in gasoline according to the present invention.
Figure 10B:
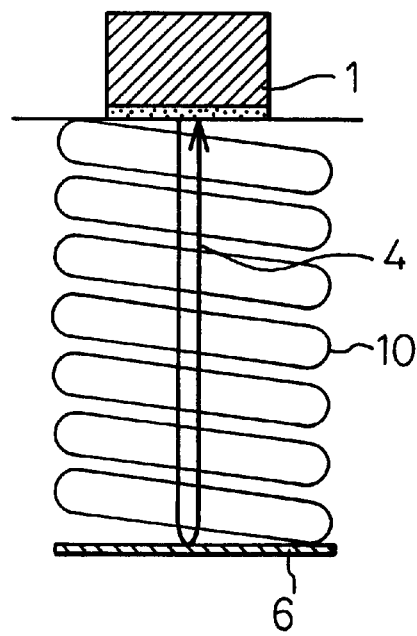
Figure 10C:
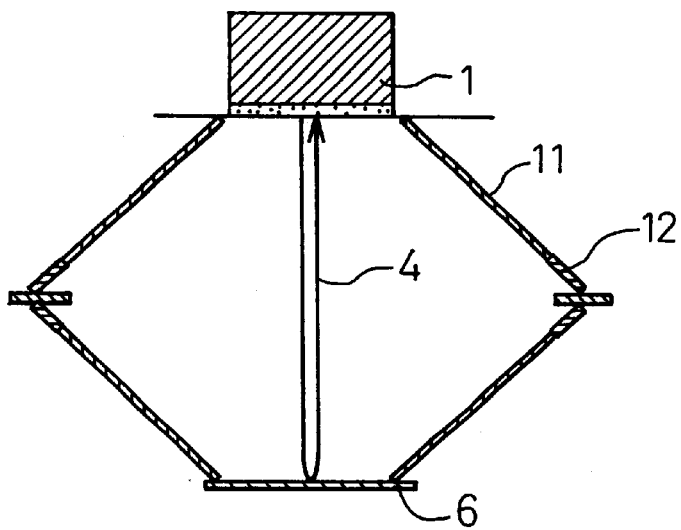

In this example, the variation of the sound velocity is cancelled by varying the propagation distance of the ultrasonic wave, as in the fourth example. An outline is illustrated in FIGS. 10(a)–10(c) and 11(a) and 11(b). First, examples of ultrasonic transducer equipment designed to compensate for a deviation from the reference temperature at the time of sound velocity measurement are shown in FIGS. 10 (b) and 10(c). The method of FIG. 10(b) uses a high thermal contraction spring 10, while the method FIG. 10(c) uses a bimetal 11. In either method, the thermal member expands or contracts with temperature to correct the propagation distance of the ultrasonic wave. More specifically, the reflecting surface attached to the high thermal contraction spring 10 or bimetal 11 changes its height according to the deviation from the reference temperature by the elastic modulus of the spring or the contraction and expansion due to the bimetallic property, and the influence of temperature is thus cancelled.

The calculation method for temperature compensation shown in FIG. 10(b) will be described in detail below.

The velocity of sound, y, at a reference temperature T is expressed as $y=-aT+b$, and at this time, the propagation time is given as $2L/-aT+b$, where L is the transducer to reflecting surface distance.

Here, consider the case where the temperature rises 1° C. from the reference temperature T.

The velocity of sound at (T+1) degrees is then written as $-a(T+1)+b$. For temperature compensation, the distance is changed so that the propagation time does not change.

The propagation distance at (T+1) degrees is $2L(-aT-a+b)/-aT+b$.

The distance from the transducer to the reflecting surface at (T+1) degrees is $L(-aT-a+b)/-aT+b$.

From this formula, the high thermal contraction spring is designed so that it contracts by $(aL/-aT+b)$ for every 1° C. rise of temperature. In this construction, since the coefficient of thermal contraction is designed to the average sound velocity in various kinds of gasolines at the reference temperature, the effect is difficult to achieve where higher accuracy is required to cancel the influence of temperature. In this design, if a gasoline with $y=-ax+c$ is considered, the velocity of sound at the reference temperature T is expressed as $-aT+C$ and the propagation speed as $2L/-aT+c$.

Here, consider the case where the temperature rises $\Delta T$ from the reference temperature T. Substituting $T+\Delta T$ for T+1 in the above formula the deviation of the sound velocity at the reference temperature is written as $(-aT+c)-[\{-a(T+\Delta T)+c\}\cdot(-aT+b)/\{-a(T+\Delta T)+b\}$; rearranging this, we have $-a(c-b)\Delta T/\{-a(T+\Delta T)+b\}$.

This shows that a deviation (error) occurs in the sound velocity at the reference temperature T.

Figure 11A:
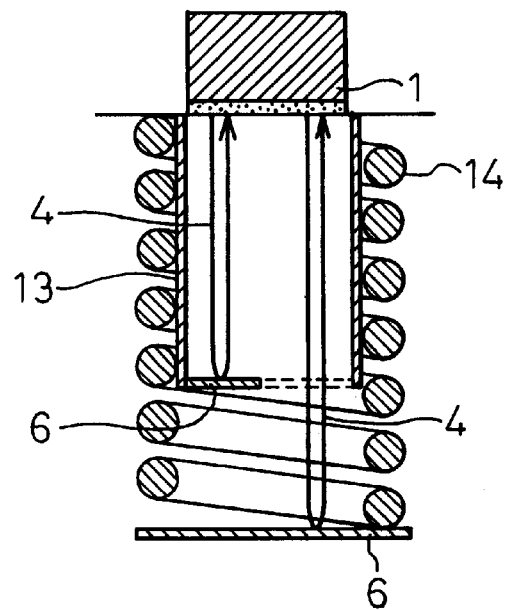
FIGS. 11(a) and 11(b) show methods for temperature-compensating the velocity of sound in gasoline with high accuracy according to the present invention.
Figure 11B:
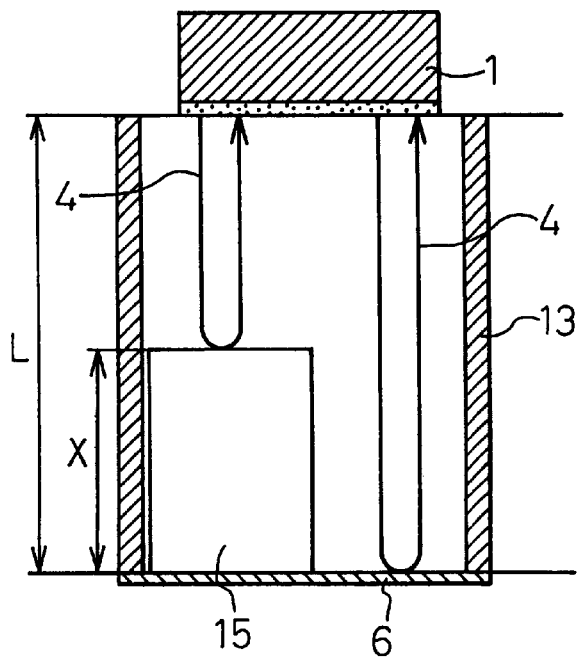

Examples of equipment designed to cancel the influence of temperature with high accuracy are shown in FIGS. 11(a) and 11(b). In FIG. 11(a), the ultrasonic waves 4 transmitted from the ultrasonic transducer 1 are reflected by reflecting surfaces on a low thermal expansion member 13 side and a high thermal expansion spring 14 side, respectively, and respective round trip times t1 and t2 are measured; then, denoting the distances to the respective reflecting surfaces by L and X, and the coefficients of thermal expansion by $\alpha h$ and $\alpha 1$, and assuming that the sound velocity is equal in both sections, calculations are performed to obtain the velocity of sound at the reference temperature 20° C. compensated for the temperature at the time of the measurement.

The detailed calculation method for temperature compensation is as follows. Denoting the temperature at the time of measurement by T and the velocity of sound in the gasoline by C, the velocity of sound at the reflecting surface on the high thermal expansion member side, $C=2X\{1+\alpha h\cdot(T-20)\}/t2$, is assumed to be equal to the velocity of sound at the reflecting surface on the low thermal expansion member side, $C=2L\{1+\alpha l\cdot(T-20)\}/t1$, and rearranging this, the velocity of sound at the reference temperature 20° C., $C_{20}=C+\Delta T\cdot$(Sound velocity–Temperature gradient), can be obtained, where $\Delta T=(X\cdot t1-Lt2)/(L\cdot t2\cdot\alpha 1-X\cdot t1\cdot\alpha h)$.

FIG. 11(b) is a diagram showing the other example of the equipment designed to cancel the influence of temperature with high accuracy. In this figure, a reflecting member 6 is secured to a low thermal expansion member 13 of length L, and a high thermal expansion member 15 of height X is mounted in an area occupying about one half of the bottom surface of the reflecting member 6. The ultrasonic waves 4 transmitted from the ultrasonic transducer 1 are reflected by the reflecting surfaces on the high thermal expansion member 15 side and the low thermal expansion member 13 side, respectively, and respective round trip times t1 and t2 are measured; then, denoting the distances to the respective reflecting surfaces by X and L, and the coefficients of thermal expansion by $\alpha 1$ and $\alpha h$, and assuming that the sound velocity is equal in both sections, calculations are performed to obtain the velocity of sound at the reference temperature 20° C. compensated for the temperature at the time of the measurement.

The detailed calculation method for temperature compensation is as follows. Denoting the temperature at the time of measurement by T and the velocity of sound in the gasoline by C, the velocity of sound in the gasoline at the reflecting surface on the low thermal expansion member side, $C=2L\{1+\alpha 1\cdot(T-20)\}/t2$, is assumed to be equal to the velocity of sound in the gasoline through the section on the high thermal expansion member side, $C=2X\{1+\alpha h\cdot(T-20)\}/t2-t1$, and rearranging this, the velocity of sound at the reference temperature 20° C., $C_{20}=C+\Delta T\cdot$(Sound velocity–Temperature gradient), can be obtained, where $\Delta T=\{L(t2-t1)-X\cdot t2\}/X\cdot t2\cdot\alpha h-L(t2-t1)\cdot\alpha 1$.

According to the present invention, since the volatility characteristics of gasoline are determined by measuring the velocity of an ultrasonic wave, the volatility can be determined with good accuracy without causing deviations as seen in the prior art when measuring the density of a gasoline containing alcohol. Furthermore, a reflection strength in a known substance is measured simultaneously with a reflection strength in the target gasoline, and thereby T50 is estimated from the acoustic impedance and sound velocity value; accordingly, the deviation due to the temperature during measurement can be easily compensated for, and an accurately corrected volatility at the reference temperature can be determined.

What is claimed is:

1. An ultrasonic-type gasoline characteristic determination apparatus for determining gasoline volatility characteristics by using an ultrasonic wave having a measured velocity, comprising:

a transducer for transmitting and receiving an ultrasonic wave in a gasoline;

distance varying means for correcting the distance between the transmission and reception of said ultrasonic wave on the basis of the temperature of said gasoline; and means for determining the volatility characteristics of the gasoline from the measured velocity of said ultrasonic wave.

2. An ultrasonic-type gasoline characteristic determination apparatus according to claim 1, including a first reflecting plate constructed from a low thermal expansion member and a second reflecting plate constructed from a high thermal expansion member, for reflecting ultrasonic waves transmitted from an ultrasonic wave transmitter, ultrasonic wave receiving means for receiving the ultrasonic waves reflected from said first reflecting plate and said second reflecting plate, means for detecting the propagation times of the waves reflected from said first reflecting plate and said second reflecting plate, and thereby obtaining velocity temperature-compensated ultrasonic wave against a reference temperature, and means for detecting the volatility characteristics of said gasoline from said temperature-compensated ultrasonic wave velocity.

* * * * *